(12) United States Patent
Smith

(10) Patent No.: US 7,041,508 B2
(45) Date of Patent: May 9, 2006

(54) POSITRON ANNIHILATION MONITOR AND METHOD FOR DETECTING HAZARDOUS MATERIALS

(75) Inventor: Gerald Smith, Scottsdale, AZ (US)

(73) Assignee: AlertTechSystems, LLC, Santa Fe, NM (US)

( * ) Notice: Subject to any disclaimer, the term of this patent is extended or adjusted under 35 U.S.C. 154(b) by 401 days.

(21) Appl. No.: 10/342,063

(22) Filed: Jan. 14, 2003

(65) Prior Publication Data

US 2003/0175982 A1  Sep. 18, 2003

Related U.S. Application Data

(60) Provisional application No. 60/354,840, filed on Feb. 6, 2002.

(51) Int. Cl.
*G01N 33/00* (2006.01)

(52) U.S. Cl. ..................................... 436/104

(58) Field of Classification Search ............. 250/358.1, 250/367, 78.03; 435/34; 436/104
See application file for complete search history.

(56) References Cited

U.S. PATENT DOCUMENTS

| 3,308,296 | A | * | 3/1967 | Cowan et al. ............... 250/366 |
| 3,593,025 | A | | 7/1971 | Grosskreutz |
| 4,463,263 | A | | 7/1984 | Padawer |
| 4,510,394 | A | | 4/1985 | Allemand et al. |
| 4,700,067 | A | | 10/1987 | Carossi et al. |
| 4,823,016 | A | | 4/1989 | Yamashita et al. |
| 4,835,390 | A | | 5/1989 | Blatchley et al. |
| 4,897,549 | A | | 1/1990 | Zerda et al. |
| 5,144,140 | A | | 9/1992 | Allyson et al. |
| 5,319,203 | A | | 6/1994 | Anderson et al. |
| 5,349,191 | A | * | 9/1994 | Rogers ....................... 250/367 |
| 5,530,245 | A | | 6/1996 | Huang |
| 5,638,166 | A | | 6/1997 | Funsten et al. |
| 5,753,914 | A | | 5/1998 | Ikegami |
| 6,043,489 | A | | 3/2000 | Tongbhoyai et al. |
| 6,178,218 | B1 | | 1/2001 | Akers et al. |
| 6,300,026 | B1 | | 10/2001 | Yamazaki et al. |
| 6,469,781 | B1 | | 10/2002 | Katz et al. |
| 6,471,136 | B1 | | 10/2002 | Chatterjee et al. |

(Continued)

OTHER PUBLICATIONS

Caffrey et al. Idaho National Engineering Laboratory, 1991 6 Pages.*

(Continued)

*Primary Examiner*—Ralph Gitomer
*Assistant Examiner*—Kailash C. Srivastava
(74) *Attorney, Agent, or Firm*—Duane Morris LLP

(57) ABSTRACT

A monitor is provided for measuring the presence of a small concentration of at least one hazardous material within a vessel. A positron source emits positrons into an annihilation region of the vessel. A plurality of species of positronium are formed from the positrons as they interact with a sample of the ambient environment disposed within the vessel. At least one gamma ray detector is located externally of the vessel for detecting gamma rays generated primarily by the absorption of the species of positronium within the annihilation region. A method is also provided where a source of positrons is arranged to direct positrons into a vessel containing a specimen of gas and a contaminant to form species of positronium. The timing of the application of positrons is sensed along with the annihilation of each of the plurality of species of positronium. The time delay between the time of application of each positron and the annihilation of the of positronium is measured to obtain a decay rate characteristic of the specimen of gas.

24 Claims, 7 Drawing Sheets

U.S. PATENT DOCUMENTS 6,791,089 B1 * 9/2004 Caffrey et al. ............ 250/358.1

OTHER PUBLICATIONS 58 page manual; Positron Annihilation Lifetime Spectroscopy PALS-1000.

7 pages extracted and adapted from: Recent Advances in Defect Characterization in 6H-SiC Using Deep Level Transient Spectroscopy and Positron Annihilation Spectroscopy; C.C. Ling, C.D. Beling, M. Gong, X.D. Chen and S. Fung; *Defects and iddfusion in semiconductors-An annual retrospective III, Defect and Diffusion Forum 183-185, Scitec Publications*, 1 (2000).

2 page Internet printout, ThermoEberline, *Automated Contamination Monitors*.

4 page Internet printout; The ROVER: Portable Gamma Ray and X-Ray Spectroscopy System; Nov. 2002.

3 page Internet printout, Positrons and Positron Spectroscopy; 2002.

5 page Internet printout, Materials Science at the LLNL Positron Facility, 2002.

*Measurements of positron-annihilation rates on molecules*; K. Iwata et al.; The American Physical Society, pp. 473-487; 1995.

2 page Internet printout; Positron Research at the Max-Planck-Institut Fur Metallforschung, Stuttgart, Germany, 1999.

5 page Internet printout; Chemical Reactions of Positron and Positronium; 1999.

2 page Internet printout; Positron Annihilation Lifetime Spectroscopy; 2002.

* cited by examiner

POSITRON ANNIHILATION MONITOR AND METHOD FOR DETECTING HAZARDOUS MATERIALS

CROSS REFERENCE TO RELATED APPLICATIONS

This application claims priority from now abandoned Provisional Patent Application Ser. No. 60/354,840, filed Feb. 6, 2002, and entitled POSITRON AIR MONITOR (PAM).

FIELD OF THE INVENTION

The present invention generally relates to hazardous material sensors, and more particularly to sensors for use in monitoring the level of hazardous contaminants in the ambient environment.

BACKGROUND OF THE INVENTION

Approximately five and three quarter million shipping containers a year, or ninety-five percent of all international origin goods, arrive in the U.S. by sea. At U.S. ports, inspecting a 20 to 40 foot long shipping container can take four customs inspectors about four hours. At that rate, often fewer than two percent are opened for inspection, and the great majority never pass through any existing sensors, e.g., x-ray machines, gamma-ray probes, or the like. In addition, U.S. borders to the north and south accommodate 125 million vehicles (including 11.2 million trucks), 2.2 million rail cars and 500 million people on an annual basis. Significantly, such prior art sensors are essentially blind to biological hazards. Front line inspectors, customs officers and other law enforcement officers have consequently called for new technology to screen shipments, whether from air, ship or rail, so that time consuming and labor intensive searches can be minimized and dangerous cargo can be prevented from entering the U.S.

Other applications include First Responders (EMT's, fire departments, and law enforcement agencies) that would benefit from an all-inclusive device to assess contaminated areas or detect hazardous materials. In addition, the device could be used for the inspection of air handling systems for "sick building syndrome" or Legionaries' disease and toxic mold in commercial and residential buildings.

There are many substances which have very small vapor pressures, but whose presence in air is nonetheless undesirable because they are very toxic or indicate the presence of unwanted substances hazardous chemicals, biological agents, explosives, drugs, etc. (hereinafter referred to as "BCA's" or Biological, Chemical Agents). Current detection methods for BCA hazards are extremely slow, and are often based upon complicated chemical or mechanical concepts, use of multi-step and labor intensive approaches, or the need for replaceable supplies (consumables). In addition, such prior art devices are often very large (not portable) and expensive.

The saturation concentrations of these hazardous substances in air at room temperature suggest that they can be detected using existing techniques. However, in the real world, they are unlikely to be presented to a detector with a sufficient volume of saturated air to make such detection easy. At best, the fraction of molecules available to a 'sniffer' will be reduced by a few orders of magnitude. Therefore, sensors must be able to detect these materials at vapor concentrations a few orders of magnitude less than their saturation concentrations.

It is well known in the art to use the anti-electron (commonly referred to as a "positron") to probe the structure of molecules. This field owes most of its existence to the study of the crystalline structure of semiconductor materials and the structure of polymers, e.g., isolation of irregularities in semiconductors and polymers. It is known that positrons of cosmic origin annihilate with extremely dilute molecular gases in interstellar space. Gamma rays that have been captured and recorded by satellites orbiting the Earth provide evidence for the existence of gases in incredibly small concentrations, and can even distinguish among various species of molecules. This technology has been further explored academically, for example, by K. Iwata et al., in their publication entitled: "Measurements of positron-annihilation rates on molecules", Physical Review A 51, 473, 1995, which publication is hereby incorporated herein by reference.

The foregoing positron annihilation method generally comprises a process in which a positron is injected into physical matter from a positron source, and the lifetime of the positron (i.e., the time between injection and annihilation) is measured to indirectly determine various characteristics of the matter. A positron is the anti-particle of an electron, and is an elementary particle having the same mass and the opposite charge as an electron. When positrons are implanted in a solid they are rapidly thermalized and annihilate with electrons. It is known that a positron and an electron briefly form an electron-positron pair (via coulomb forces) when the two particles meet in a molecular crystal or in an amorphous solid material, and then the pair annihilates. The positron-electron pair behaves in a manner similar to a particle in a bound state, and is referred to as "positronium."

When positronium annihilates, two or three annihilation gamma-rays are emitted. There are two types of positronium, para-positronium and ortho-positronium. The spins of the electron and the positron are anti-parallel in the para-positronium and parallel in the ortho-positronium. Para-positronium decays into two 511 kiloelectronvolt (keV) gamma rays, one in each of two directions with an angel of 180° between them. Ortho-positronium decays into three gamma rays, the sum energy of which is 1022 keV. While the lifetime of a para-positronium pair is about 0.13 nanoseconds (ns), the lifetime of an ortho-positronium pair depends upon the electron density in the surroundings of the positronium. The mean lifetime of ortho-positronium in vacuum is about 140 ns, when it is annihilated in a self-annihilation process. However, the lifetime decreases down to the range from about 1 to about 5 ns when an ortho-positronium pair annihilates through a "pick-off" process in which the positronium takes electrons from the surrounding matter. With the aforementioned positron annihilation method, a positron lifetime is determined by measuring the time variation in intensity of the annihilation gamma-rays emanating from the material into which the positrons had been injected.

The use of ortho-positronium decay is known for the determination of the location and size of crystal lattice defects. For example, when ortho-positronium exists in a vacancy-type defect, the measured lifetime of the ortho-positronium correlates well with the size of the defect. With increases in the size of the vacancy-type defect, the probability that the ortho-positronium will succumb to "pick-off" annihilation with an electron oozed out from the inner wall of the defect decreases, resulting in longer lifetimes of the ortho-positronium. Thus, the size of the defect can be determined by measuring the lifetime of the ortho-positronium. It is also known, however, that the lifetime of ortho-positronium tends to saturate when the radius of the defect increases beyond a certain value, e.g., about 0.5 nanometers (nm) so that the maximum value of the radius of a defect measurable by this method is about 0.5 nm.

There is a need in the art for an improved method and apparatus for sensing and monitoring the ingress of so called hazardous BCA materials into the United States of America. It would be of benefit if the foregoing positron annihilation method could be used to detect such hazardous BCA materials.

SUMMARY OF THE INVENTION

The present invention provides a device for measuring the presence of a small concentration of at least one hazardous material within a vessel. A positron source emits positrons into an annihilation region of the vessel that is spaced apart from the positron source. A plurality of species of positronium are formed from the positrons as they interact with a sample of the ambient environment, e.g., an ambient air sample, disposed within the vessel. The annihilation region within the vessel is positioned such that at least a portion of the sample to be monitored must pass in annihilation proximity of the positrons so as to form at least one of the species of positronium. Two gamma ray detectors are located externally of the vessel, and shielded from the positron source, for detecting gamma rays generated primarily by the absorption of the species of positronium within the annihilation region.

In another embodiment of the invention, a device for measuring the constituents of a gaseous sample is provided that includes a source of positrons which positrons are deposited within an annihilation region of a vessel. The annihilation region is spaced apart from the positron source and also contains the gaseous sample. A plurality of positronium species are formed through interaction of the positrons with the gaseous sample. Two gamma ray detectors are disposed adjacent to the annihilation region for detecting gamma rays generated by the decay of the species of positronium within the annihilation region.

A method for detecting contaminants in a specimen containing at least one known gas is also provided where a source of positrons is arranged so as to direct positrons into a vessel containing a specimen of the at least one known gas and at least one contaminant so as to form a plurality of species of positronium. The timing of the application of the positrons to the vessel is sensed along with the annihilation of each of the plurality of species of positronium in the vessel. The time delay between the time of application of each positron to the vessel and the annihilation of at least one species of positronium is measured to obtain a decay rate characteristic of the specimen of gas, each time delay being measured over a substantial time scale, the time scale for determining each time delay being in the range from about 1 ns to about 15 ns. The contaminants within the specimen of gas are then determined as a function of the decay rate of the at least one species of positronium.

BRIEF DESCRIPTION OF THE DRAWINGS

These and other features and advantages of the present invention will be more fully disclosed in, or rendered obvious by, the following detailed description of the preferred embodiments of the invention, which are to be considered together with the accompanying drawings wherein like numbers refer to like parts and further wherein.

DETAILED DESCRIPTION OF THE PREFERRED EMBODIMENT

Figure 1:
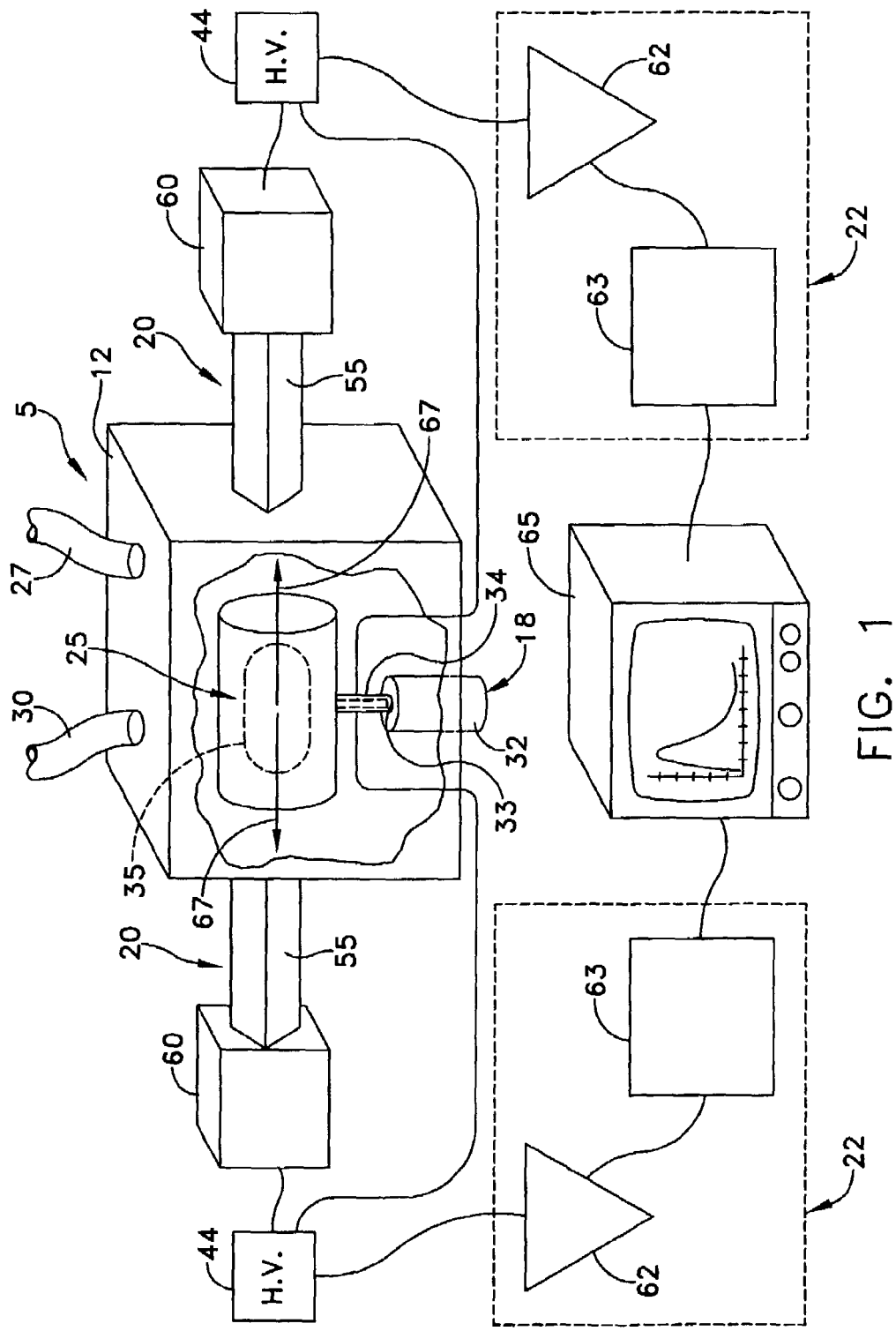
FIG. 1 is a schematic perspective view of an apparatus formed in accordance with the present invention for measuring the presence of a small concentration of at least one hazardous material in a sample of ambient atmosphere.

This description of preferred embodiments is intended to be read in connection with the accompanying drawings, which are to be considered part of the entire written description of this invention. The drawing figures are not necessarily to scale and certain features and atomic structures formed by the method of the invention may be shown highly exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. In the claims, means-plus-function clauses are intended to cover the structures described, suggested, or rendered obvious by the written description or drawings for performing the recited function, including not only structural equivalents but also equivalent structures.

Figure 2:
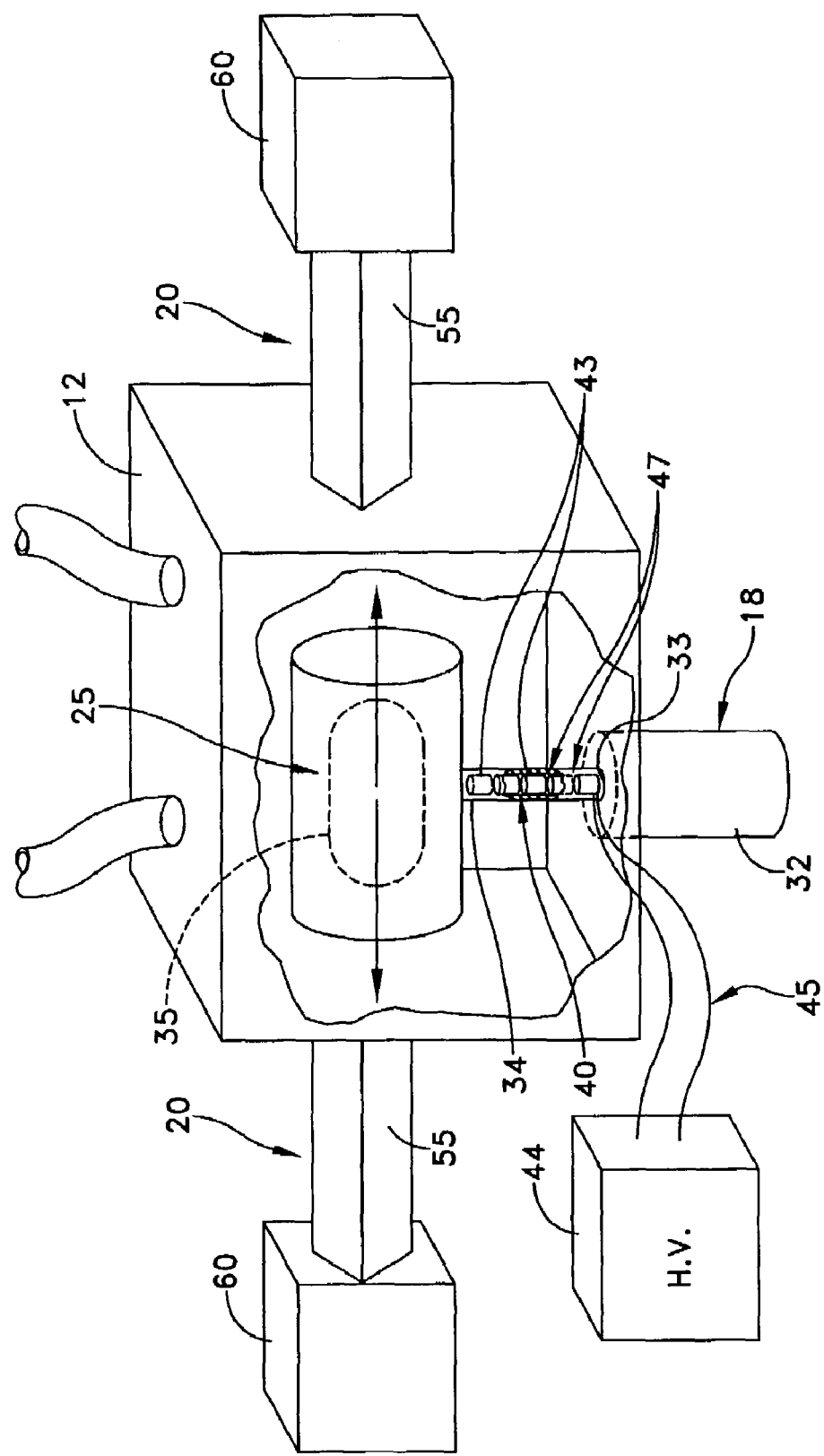
FIG. 2 is a schematic perspective view, similar to FIG. 1, having the signal processing and storing systems removed for clarity of illustration.
Figure 3:
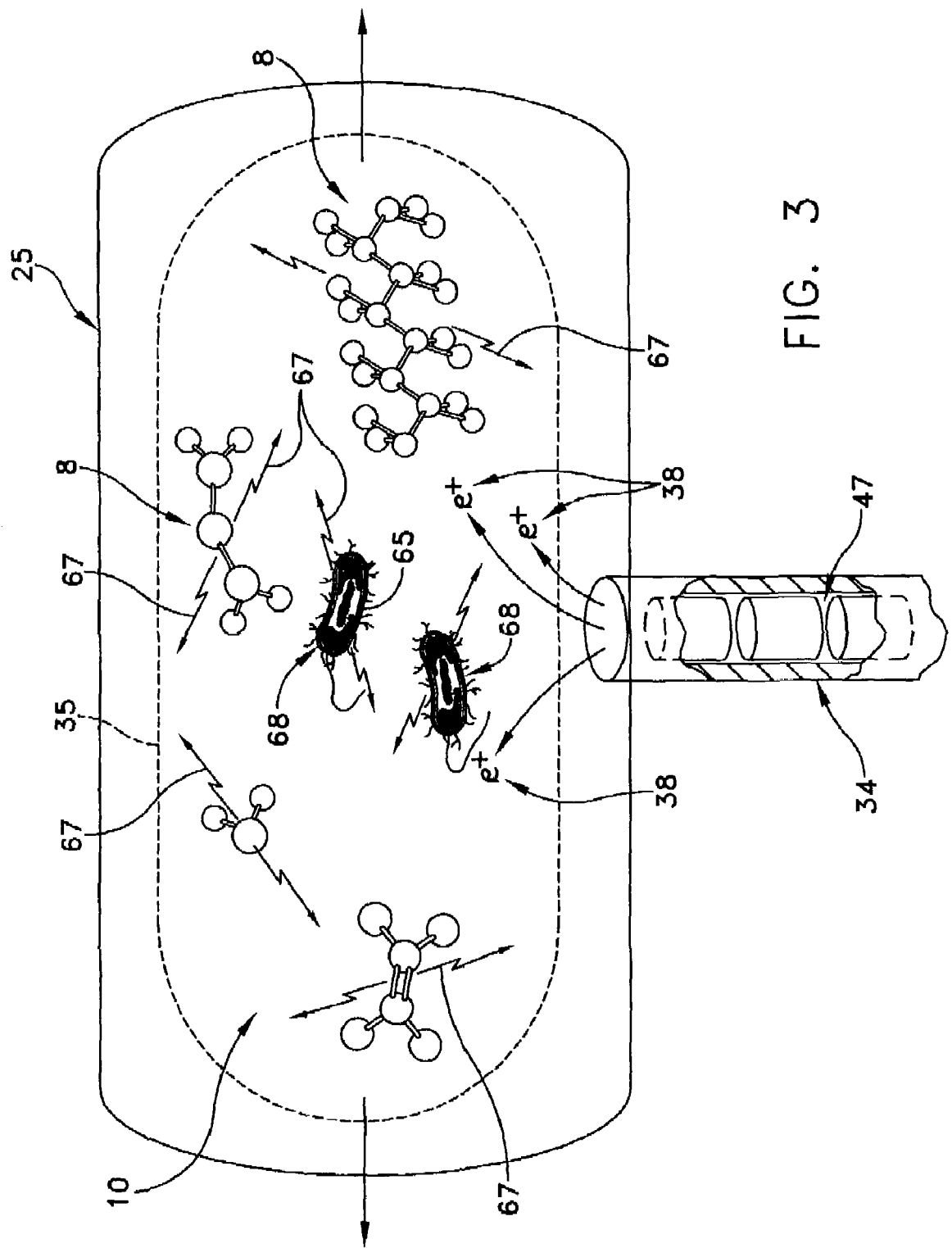
FIG. 3 is a stylized illustration of various molecular and biological structures that may be present within an annihilation region of a vessel portion of the present invention.
Figure 5:
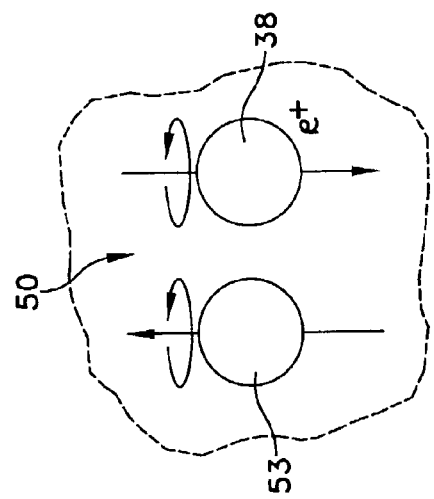
FIG. 5 is a stylized illustration of a para-positronium electron-positron pair.
Figure 6:
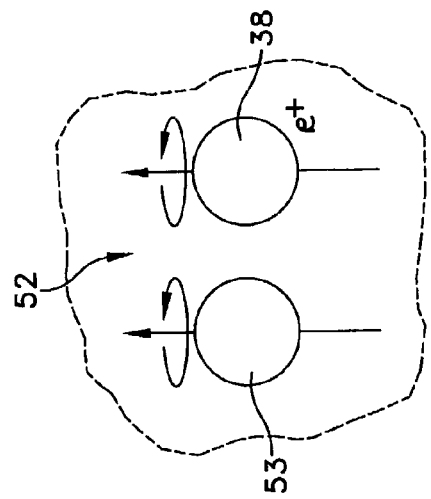
FIG. 6 is a stylized illustration of an ortho-positronium pair.
Figure 4:
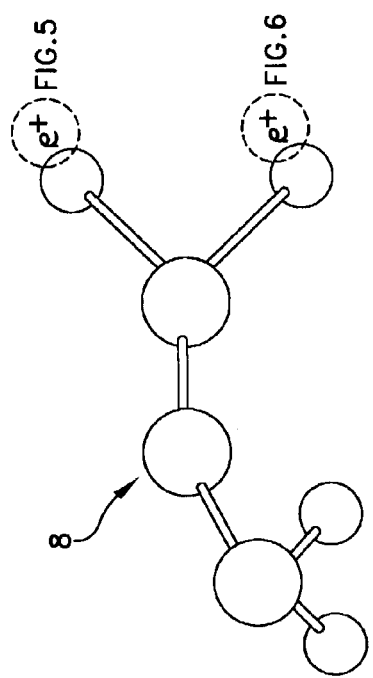
FIG. 4 is a stylized illustration of a hazardous material molecule having species of positronium formed in association with atomic structures of the molecule.
Figure 7:
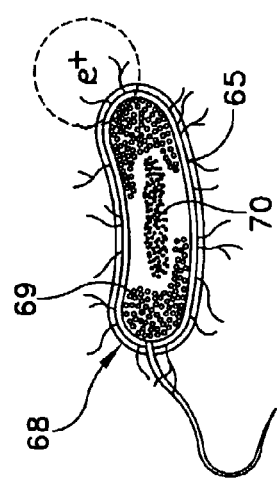
FIG. 7 is a stylized illustration of a bacterium having a species of positronium formed with a portion of its molecular structure.
Figure 8:
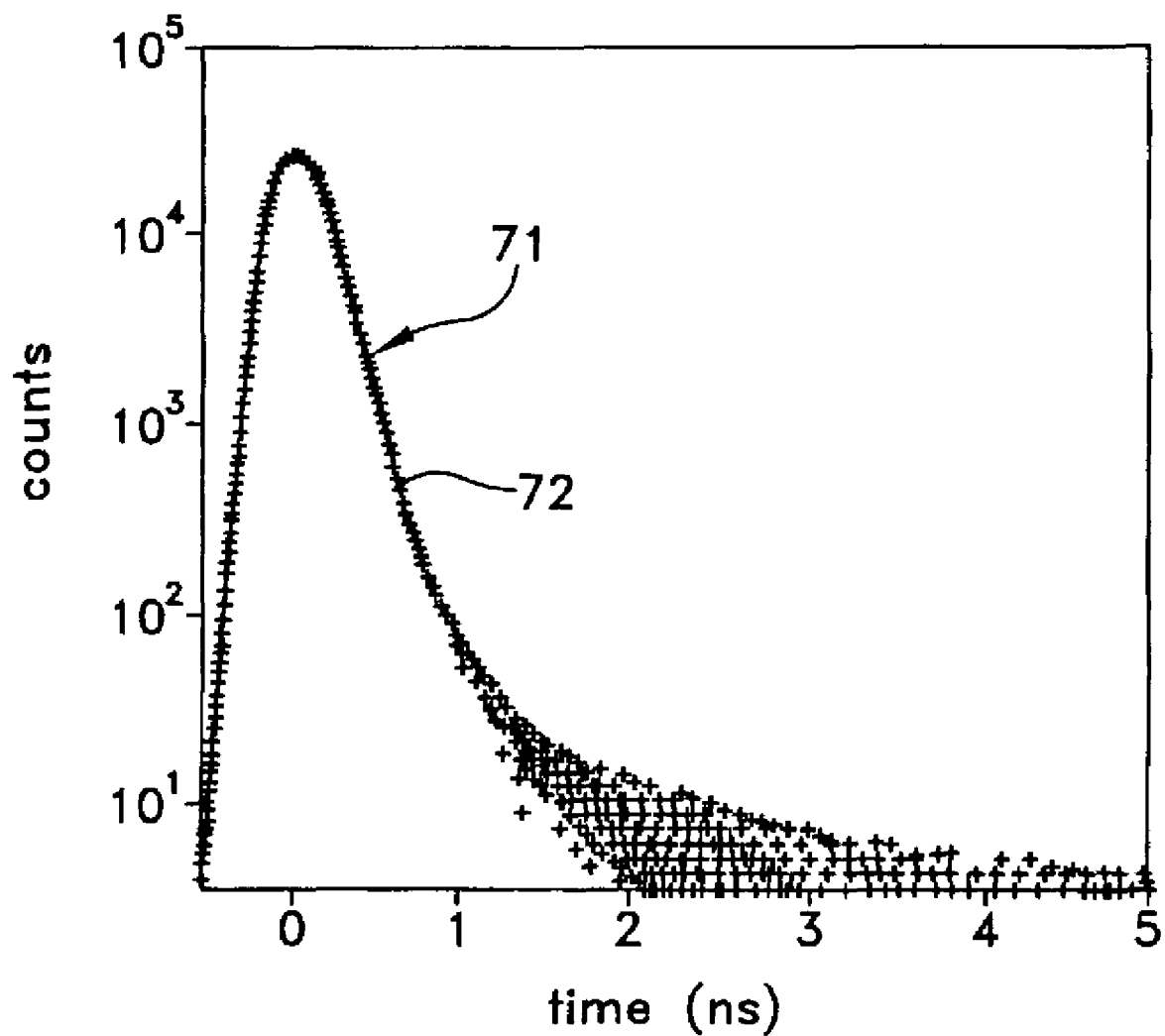
FIG. 8 is a graphic representation of a positron-lifetime curve of the type formed by the method of the present invention.
Figure 9:
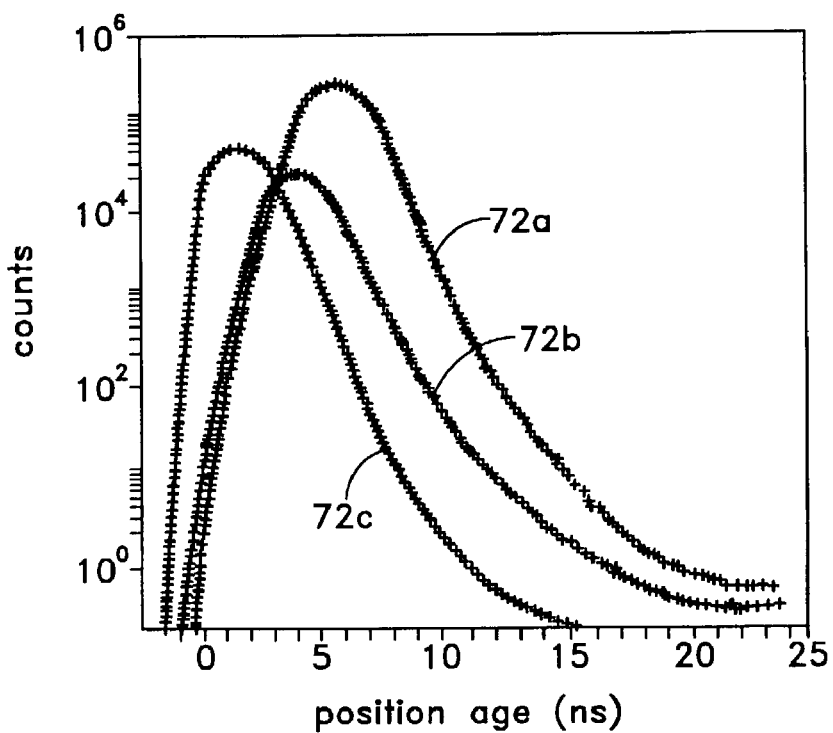
FIGS. 9 and 10 are graphic representations of signature-curves of the type resulting from the practice of the present invention.
Figure 10:
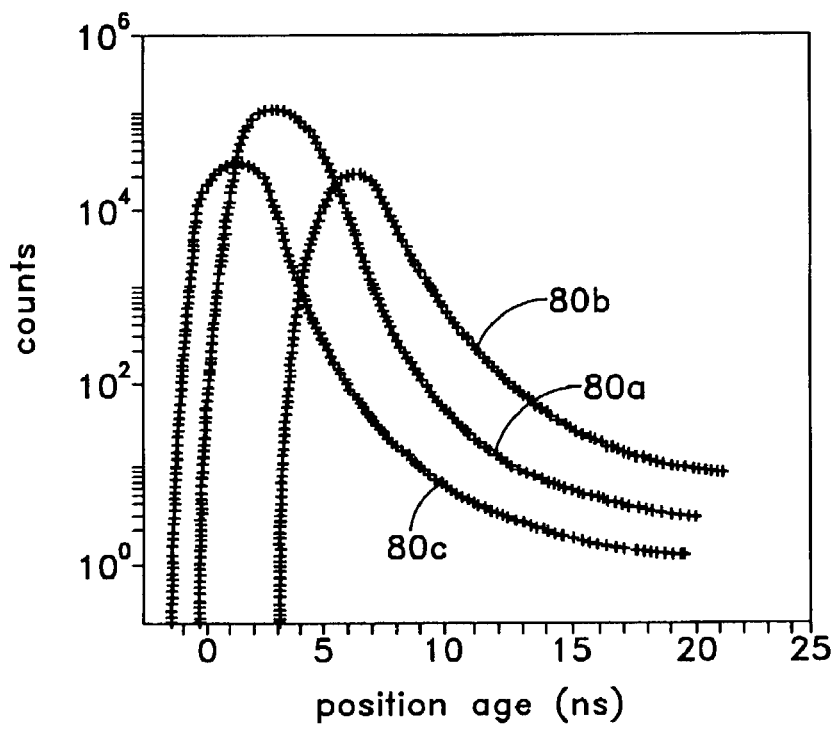
Figure 11:
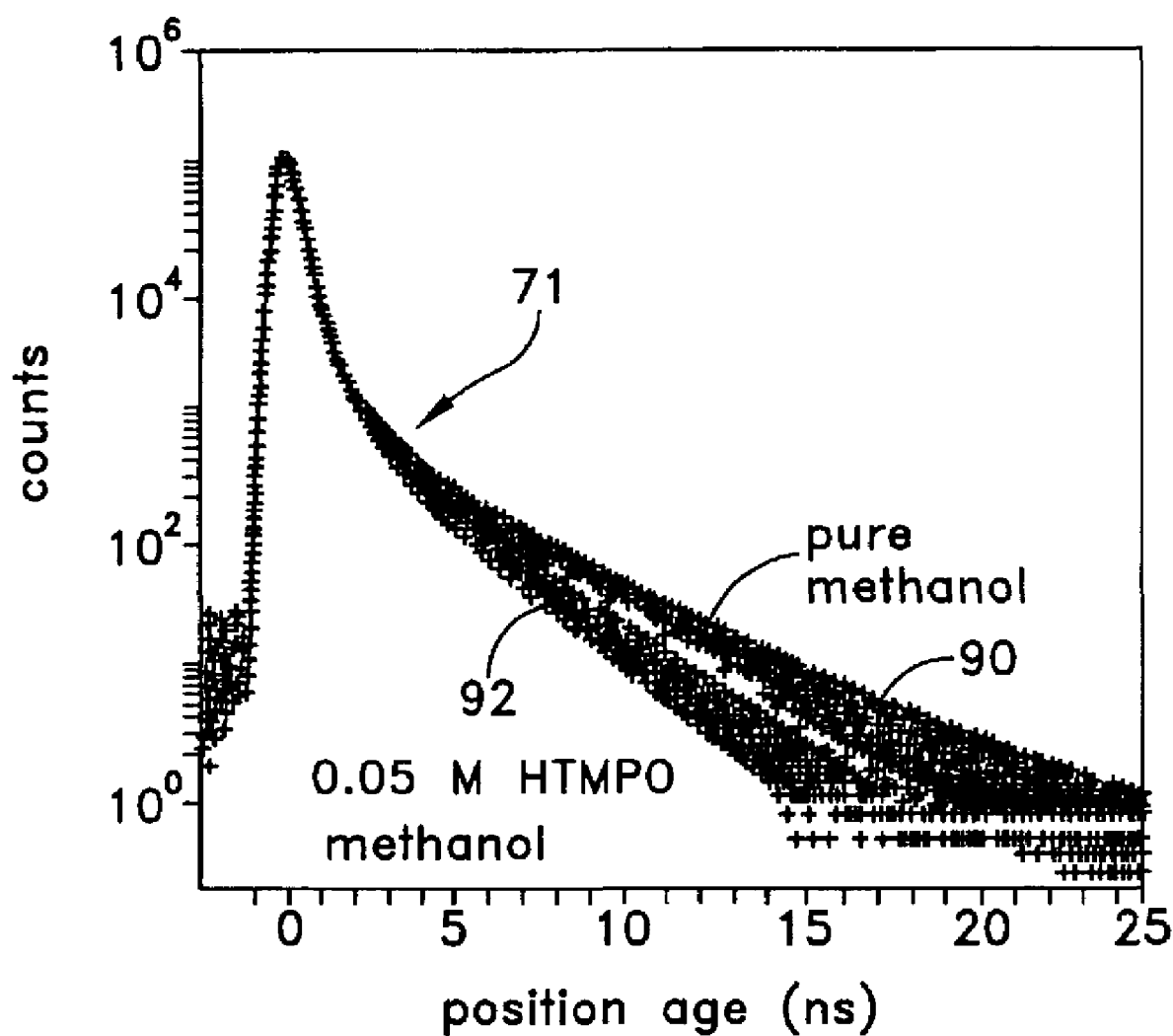
FIG. 11 is a graphic illustration of two signature curves, one for pure methanol and one for methanol with a small admixture of HTMPO.

Referring to FIGS. 1, 2, and 3, the present invention provides an air monitor 5 and method for monitoring BCA contaminants 8 in a specimen of ambient air 10. It should be noted that a positron-based detection device differs from most radiometric monitoring systems, such as alpha ray and beta particle systems, since it measures the absorption of positrons which characteristically are associated with the generation of a pair of gamma rays. Thus, while positrons are very sensitive to changes in the media through which they flow, the gamma-ray photons which are generated from an annihilation event have good penetrating properties and may be readily detected through relatively thick walls.

More particularly, air monitor 5 generally comprises an air measurement vessel 12, a positron source 18, gamma-ray detectors 20, and a signal processing and storing system 22. Measurement vessel 12 defines an interior chamber 25, and includes an entrance port 27 and an exit port 30 that are formed in the wall of measurement vessel 12 so that ambient air sample 10 (FIG. 3) may be deposited within the vessel for analysis. A variety of metals, ceramics, and polymers that are suitable for maintaining a partial vacuum may be used to form vessel 12.

Positron source 18 is preferably a ten microCurie (μCi) source whose ionizing radiation output is within present and future federally mandated limits for safe handling, e.g., $^{22}$Na with a 2.6 yr. half-life. Of course, other sources of positrons, e.g., $^{44}$Ti/$^{44}$Sc (49 yr.), $^{58}$Co (70.8 day), or $^{68}$Ge/$^{68}$Ga (271 day), may also be used in connection with the present invention. Positron source 18 is typically housed in a container 32 that allows for appropriate shielding so that the majority of positrons are released from an exit port 33 into a transfer conduit 34. It will be understood that in order to precisely monitor the annihilation events, gamma ray detectors 20 should be collimated to exclude radiation from positron source 18, since most positron sources also emit gamma rays. An annihilation region 35 within measurement vessel 12 is spaced apart from positron source 18. Positrons 38 (identified by reference character "e+") are generated by positron source 18 and directed through transfer conduit 34 so as to be transferred into annihilation region 35 of interior chamber 25 by, e.g., an electrostatic or magnetic lens assembly 40 (FIG. 2). Of course, it will be understood that positron source 18 may be housed within measurement vessel 12 so that positrons 38 simply enter annihilation region 35 as a result of natural decay and scattering processes.

Electrostatic or magnetic lens assembly 40 is adapted to be sealingly mounted to positron source 18, via exit port 33, and may take several forms. For example, electrostatic or magnetic lens assembly 40 may comprise a plurality coaxially aligned, cylindrical tubes 43 that are formed from a highly conductive metal, e.g., copper or its alloys, or highly magnetic metals, e.g., SmCo, NdFeB or the like. For an electrostatic version of lens assembly 40, tubes 43 are individually interconnected to a source of variable high voltage electrical potential 44 in a manner well known to those of ordinary skill in the art (e.g., cables 45). For a magnetic version of lens assembly 40, one or more tubes 43 would comprise a permanent magnet. In either case, tubes 43 are sized so as to fit within transfer conduit 34 arranged between positron source 18 and interior chamber 25. For an electrostatic version of lens assembly 40, gaps 47 are defined between predetermined groups of tubes 43 so as to form strong electric field gradients adjacent to the edge portions of the tubes that are positioned on either side of a gap 47. Electrostatic or magnetic lens assembly 40 normally does not extend into measurement vessel 12, although it may do so, as needed, for a particular design purpose. Both transfer conduit 34 and interior chamber 25 are maintained at a similar partially evacuated state, i.e., internal pressure, as positron source 18.

A plurality of species of positronium are formed from the interaction of positrons 38 with at least BCA contaminants 8 in ambient air sample 10. In particular, at least a population of para-positronium 50 (anti-parallel spins) and ortho-positronium 52 (parallel spins) are formed within measurement vessel 12 in which an electron 53 from a molecule of an BCA contaminant 8, e.g., a molecule of a hazardous material or a molecule that is resident within the cell wall of a living pathogenic organism, is paired with a positron 38 (FIGS. 4–7). Annihilation region 35 is located within interior chamber 25, and positioned such that at least a portion of the sample of ambient air 10 to be examined must pass in positron capture proximity of at least one positron 38.

Referring again to FIGS. 1 and 2, gamma ray detectors 20 are externally located relative to measurement vessel 12, and are often shielded from positron source 18. Gamma ray detectors 20 sense 511 keV gamma rays 67 generated by the absorption of the species of positronium within annihilation region 35. In a particularly advantageous embodiment of the present invention, gamma-ray detectors 20 comprise an array of photodetectors consisting of scintillator crystals 55 coupled to photomultiplier tubes 60 (PMTs). When a photon strikes a detector 20, it produces light in one of scintillator crystals 55 that is then sensed by PMT 60, which registers the event (count) by passing an electronic signal to reconstruction processing circuitry comprising a pre-amplifier 62 and a multichannel analyzer 63. The counts are stored in a database, and may be displayed on a conventional computer controlled display monitor 65. Scintillator crystals 55 must have certain properties, among which are (1) good stopping power, (2) high light yield, and (3) fast decay time. Stopping power is the ability to stop the 511 keV gamma-ray photons 67 (FIG. 3) in as little material as possible so as to reduce the overall size of the photodetector, of which the scintillator crystals form a substantial portion.

It has been found that scintillator crystals formed from barium fluoride (BaF$_2$) are particularly well suited to the present invention. The use of BaF$_2$ as a scintillator material is described in Allemand et al., U.S. Pat. No. 4,510,394, which patent is incorporated herein by reference. BaF$_2$ emits light having two components: a slow component having a decay constant of approximately 620 ns and a fast component having a decay constant of approximately 0.6 ns. The fast component of BaF$_2$ emits light in the ultraviolet region of the spectrum. Glass photomultiplier tubes are often transparent to ultraviolet light, so a quartz photomultiplier tube is preferred for detecting the fast component of BaF$_2$. The fast component gives BaF$_2$ very good timing resolution. Since BaF$_2$ is not hygroscopic, it is quite suitable for use in many high humidity locations, e.g., seaports, outdoors, etc. The stopping power of BaF$_2$ with respect to gamma-ray photons is higher than that of other well known scintillator materials, e.g., sodium iodide and cesium iodide. Moreover, BaF$_2$ is substantially insensitive to water, as well as to numerous organic solvents such as ethanol, ethyl ether, acetone and methanol. In addition, it can be easily machined or worked, e.g. compared with glass which is harder, but it is still not fragile.

Referring now to FIGS. 3 and 8–11, the inverse lifetime or natural width Γ(decay rate expressed in decays per second), of a positron in a gas is generally expressed as: $\Gamma = \pi r_o^2 c n\, Z_{\mathit{eff}}$, where $r_o$ and c are constants, and are the classical electron radius and speed of light, respectively, n is the gas density, and $Z_{\mathit{eff}}$ is the "effective" atomic number of the gas molecule. Thus, the physics of the process of the present invention is embodied in one number, $Z_{\mathit{eff}}$. Significantly, Γ is not proportional to the atomic number of a molecule. It has been found that large molecules exposed to positrons generate annihilations at a relatively faster rate than small molecules. In other words, $Z_{eff}$ grows more rapidly than Z, especially as Z gets large. The decay rate may grow by about a factor of one thousand with every advance of the atomic number by a factor of ten.

For example, assuming that the decay rate for positrons 38 exposed to hydrogen molecules (Z=2) is one (in arbitrary units), then the decay rate in the presence of anthracene ($C_{14}H_{10}$, Z=94) is about four million. By calibrating the present invention for $Z_{eff}$ for the BCA's in question, they may be detected in ambient air sample 10. Hence, the lifetime of complex molecular structures, e.g., the cell wall 65 of a bacterium 68 that is itself built up from many complex molecular structures, including proteins 69 and DNA 70, etc., each with a unique $Z_{eff}$, are expected to be very short. On average, the lifetimes of positrons that are paired with complex molecular structures is often approximately several thousands of times less than the $Z_{eff}$ for molecular oxygen and nitrogen, which are the primary constituents of ambient air sample 10). By selection and measurement of a characteristic slope in a lifetime distribution, air monitor 5 allows for the identification of macromolecules, and their different species, from the background of annihilations on light atoms and molecules normally found in air. These light atoms and molecules include oxygen, nitrogen, inert gases, nitrous and carbon oxides from automobiles, power plants, airplanes and other fossil fuel burning machines, pesticides, naturally and artificially occurring dusts, etc.

The average lifetime of each positron species 50,52 is measured by observing and recording the positron annihilation generated gamma rays 67 with gamma-ray detectors 20. A positron-lifetime curve 71 is created based on annihilation gamma rays 67, after accumulating tens of thousands of counts over time (FIG. 8). Advantageously, when the counts are graphed as a function of time, a unique signature-curve 72 is revealed for each particular molecular constituent in the sample of ambient air 10 (FIGS. 8–10). The slope of each signature-curve 72*a*, 72*b*, 72*c*, etc., is a measure of the mean lifetime, or age, of the ortho-positronium state formed with an electron 53 from a given molecular constituent (FIG. 9). Computer system and display 65 of the type well known in the art may be employed to deconvolute the aggregate positron age curves 72*a*–*c* into their constituent parts. A data base is provided that contains an extensive library of individual BCA signature-curves 80*a*, 80*b*, 80*c*, etc., as well as signature-curves for common background distractions, e.g., commonly found molecular constituents of ambient air at a particular location (FIG. 10). Signature-curves 72 are then compared to the BCA signature-curves 80 so as to determine the type and quantity of BCA molecules 8 in ambient air sample 10.

It should be understood that the positron age method is a physical characterization of the molecular mass, and hence size, of a chemical or biological agent. It is not a chemical characterization, such as would be developed by observing the fluorescence of molecules under irradiation with laser light. In this sense, it is similar in output to the well known mass spectrometer method where the device renders the charge to mass ratio (g/m) of the sample. However, since the positron age measurement performed by air monitor 5 does not need to differentiate between different charge states of a molecule, it is intrinsically simpler than a mass spectrometer.

The present invention may be employed to identify extremely small concentrations of chemical and/or biological agents in air. Referring to FIG. 11, upper curve 90 shows the results (counts per unit time) for pure methanol, (atomic number "Z"=18; and lower curve 92 shows the results for pure methanol with a very small admixture of HTMPO, (Z=65). The separation of the two curves and their different slopes is indicative of the improved sensitivity for identifying a unique molecular species when practicing the present invention, that is comparable to, or better than prior art techniques at less than a few parts per million concentrations of BCA's. It is important to note, for example, that the chemical composition of four nerve agents (Tabun, Sarin, Soman and VX) have marked similarities to HTMPO. Both contain significant C—H and $CH_3$—N bonds. These nerve agents are somewhat heavier (average molecular wt. ~180, vs. 112 for HTMPO) due to phosphorous and fluorine bonds, and thus display unique positron annihilation lifetime signature-curves 80.

In operation, samples of air 10 are exposed to positrons 38 in measurement vessel 12. Including a 20% detector geometrical acceptance for each of two gamma ray detectors 20, the total counting rate would be $3.7\times10^5$ (10 microCi) decays/sec×2×0.2=148 kHz. These events are almost exclusively the two gamma ray decay mode of para-positronium 50 states, constituting a sharp peak for times less than ~2 ns. These events are considered background in detector 20. Including an efficiency of 1% for conversion of positrons into long-lived ortho-positronium 52 states, this gives a counting rate of 3.7×105 decays/sec×2×0.2×0.01=1.48 kHz. These events are the signal events (at times greater than ~2 ns), from which the desired lifetime measurement is determined.

In nuclear counting situations, background rates must be considered. It is well known that the main source of background radiation comes from free or para-positronium annihilations on the walls of measurement vessel 12 or the gas itself, resulting in two back-to-back gamma rays 67 of 511 KeV energy each. Recorded times for primary gamma rays 67 from such background are often well under a few nanoseconds (ns). Some primary gamma-rays 67 will scatter off electrons in the walls of vessel 12 or the gas making up most of ambient air sample 10, and "bounce" around the interior chamber 25 before annihilating, resulting in delayed times. If, for example, the dimensions of interior chamber 25 are approximately 10 cm on average, and the speed of gamma rays is $3\times10^{10}$ cm/second, then one traversal of interior chamber 25 takes only about 0.33 ns. Hence, a delay of 10 ns would require 33 scatters to achieve.

It is to be understood that the present invention is by no means limited only to the particular constructions herein disclosed and shown in the drawings, but also comprises any modifications or equivalents within the scope of the claims.

What is claimed is:

1. A device for measuring constituents of a gaseous sample comprising:

a no more than ten μCurie source of positrons;

an annihilation region spaced apart from said source and occupied by said gaseous sample, wherein at least one positronium species is formed through interaction of said positrons with said gaseous sample;

two gamma ray detectors disposed adjacent to said annihilation region for detecting gamma rays generated by the decay of said at least one species of positronium within said annihilation region;

wherein gamma rays emitted from a single sample are detected by said two detectors.

2. A measuring device according to claim 1, wherein said annihilation region is disposed within an interior chamber of a vessel having walls, and includes an entrance port and an exit port that are formed in at least one of said walls to deposit an air sample within said vessel.

3. A measuring device according to claim 2, wherein said annihilation region within said vessel is spaced apart from said source of positrons.

4. A measuring device according to claim 2, wherein positrons from said positron source are passed through a transfer conduit into said annihilation region by at least one of an electrostatic lens assembly and magnetic lens assembly.

5. A measuring device according to claim 4, wherein an electrostatic lens assembly is sealingly mounted to said positron source and comprises a plurality of coaxially aligned cylindrical tubes that are individually interconnected to a source of variable high voltage electrical potential and arranged between said source of positrons and said interior chamber with gaps defined between groups of said tubes so as to form strong electric field gradients adjacent to the edge portions of said tubes that are positioned on either side of a gap.

6. A measuring device according to claim 5, wherein said source of positrons, said transfer conduit and said interior chamber are maintained at a constant partially evacuated state.

7. A measuring device according to claim 1, wherein said positron source comprises $^{22}$Na.

8. A measuring device according to claim 1, wherein said positron source is elected from the group consisting of $^{44}$Ti, $^{44}$Sc, $^{58}$Co, $^{68}$Ge, and $^{68}$Ga.

9. A measuring device according to claim 1, wherein said constituent of said gaseous sample is positioned within said annihilation region such that at least a portion of said sample passes in positron capture proximity of at least one positron.

10. A measuring device according to claim 1, wherein said at least one gamma ray detector is located in a spaced annihilation region shielded from said positron source.

11. A measuring device according to claim 1, wherein said at least one gamma ray detector comprises scintillator crystals formed from barium fluoride.

12. A measuring device according to claim 1, wherein said at least one gamma ray detector comprises cesium fluoride.

13. A measuring device according to claim 1, wherein an average lifetime of said at least one positronium species is measured by observing and recording positron annihilation generated gamma rays with said at least one gamma-ray detector.

14. A measuring device according to claim 13, wherein said average lifetime of said at least one positronium species is displayed upon display means as a positron-lifetime curve.

15. A measuring device according to claim 14, wherein said positron-lifetime curve is directly related to a count of positron annihilation gamma rays as a function of time which yields a unique signature-curve for each molecular constituent in said gaseous sample.

16. A measuring device according to claim 14, wherein the slope of said signature-curve represents a measure of the mean lifetime of said at least one species of positronium formed within said annihilation region from an electron from a molecule of a constituent of said gas sample that is paired with one of said positrons.

17. A device for measuring constituents of a gaseous sample comprising:
a source of positrons;
an annihilation region spaced apart from said source and occupied by said gaseous sample wherein at least one positronium species comprising a population of ortho-positronium is formed through interaction of said positrons with said gaseous sample; and
two gamma ray detectors disposed adjacent to said annihilation region for detecting gamma rays generated by the decay of said at least one species of positronium within said annihilation region.

18. A measuring device according to claim 17, wherein each member of said population of ortho-positronium is formed within said annihilation region from an electron from a molecule of a constituent of said gas sample that is paired with one of said positrons.

19. A measuring device according to claim 18, wherein said molecule comprises a portion of a biological or chemical material.

20. A measuring device according to claim 18, wherein said molecule comprises a portion of an organism, or molecule.

21. A measuring device according to claim 18, wherein said molecule comprises a portion of a nerve agent.

22. A measuring device according to claim 18, wherein said molecule comprises a portion of a chemical warfare agent.

23. A device for measuring constituents of a gaseous sample comprising:
a source of positrons;
an annihilation region spaced apart from said source and occupied by said gaseous sample, wherein at least one positronium species is formed through interaction of said positrons with said gaseous sample; and two gamma ray detectors disposed adjacent to said annihilation region for detecting gamma rays generated by the decay of said at least one species of positronium within said annihilation region, wherein at least one gamma ray detector is substantially insensitive to water.

24. A device for measuring the presence of a small concentration of at least one hazardous material within a vessel having walls comprising:
a positron source;
an annihilation region spaced apart from said positron source for receiving positrons from said positron source and wherein at least one species of positronium comprising a population of ortho-positronium is formed by an interaction of said positrons with said at least one hazardous material, said annihilation region being located within said walls of said vessel and being positioned such that at least a portion of said at least one hazardous material to be measured passes within positron-capture-proximity of said positrons.

* * * * *